United States Patent
Punyani et al.

(10) Patent No.: US 10,406,094 B2
(45) Date of Patent: *Sep. 10, 2019

(54) COMPOSITION FOR FAST DRY OF HAIR

(71) Applicant: The Procter & Gamble Company, Cincinnati, OH (US)

(72) Inventors: Supriya Punyani, Singapore (SG); Lisa Jo Bartz, Singapore (SG); Jennifer Mary Marsh, Deerfield Township, OH (US); Erica Vencil Buckner, Singapore (SG); Andreas Flohr, Kronberg (DE); Brian Xiaoqing Song, Mason, OH (US); Yonas Gizaw, West Chester, OH (US); Ioannis Constantine Constantinides, Wyoming, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/473,832

(22) Filed: Mar. 30, 2017

(65) Prior Publication Data

US 2017/0281523 A1 Oct. 5, 2017

Related U.S. Application Data

(60) Provisional application No. 62/316,852, filed on Apr. 1, 2016.

(51) Int. Cl.
*A61K 8/898* (2006.01)
*A61K 8/41* (2006.01)
(Continued)

(52) U.S. Cl.
CPC ............. *A61K 8/898* (2013.01); *A61K 8/19* (2013.01); *A61K 8/34* (2013.01); *A61K 8/342* (2013.01);
(Continued)

(58) Field of Classification Search
None
See application file for complete search history.

(56) References Cited

U.S. PATENT DOCUMENTS

| | | | |
|---|---|---|---|
| 2,392,314 | A | 1/1946 | Dalton |
| 4,329,097 | A | 5/1982 | Steele et al. |

(Continued)

FOREIGN PATENT DOCUMENTS

| | | |
|---|---|---|
| DE | 19536423 A1 | 4/1996 |
| DE | 1020011089357 A1 | 8/2012 |

(Continued)

OTHER PUBLICATIONS

Watson, "5 Hair Conditioners You can Make At Home", [retrieved from on-line website: www.wisebread.com, pp. 1-11, 2011]. (Year: 2011).*

(Continued)

*Primary Examiner* — Ernst V Arnold
(74) *Attorney, Agent, or Firm* — Linda M. Sivik

(57) ABSTRACT

The present invention discloses a hair conditioner composition comprising
a) from about 0.15% to about 16% moisture control material or mixtures of moisture control materials wherein one or more moisture control material is selected from the group containing:
i. Class I Moisture Control Material having the structure selected from:

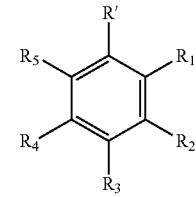

wherein R' is —COOY, sulfonic acid, or —C═CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH═CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;

ii. Class IIa having the structure selected from:

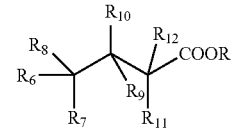

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;

iii. Class IIb having the structure selected from:

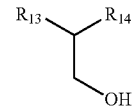

(Continued)

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;
iv. Class IIc being an alcohol comprising an unsaturated double bond in the C2 position;
v. Class IId being an alkyl-substituted glycol wherein the structure of such alkyl substituted glycol contains less than 20 carbon atoms;
vi. Class IIe being a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;
vii. Class IIf having a structure the structure selected from:

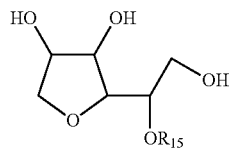

wherein $R_{15}$ could be hydrogen, alkyl, alkenyl, phenyl group and wherein the structure of the $R_{13}$ group contains less than 20 carbon atoms;
viii. Class IIg being a fatty acid ester containing from 15-40 total carbon atoms; and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4;
b) from about 0.1% to about 12% of one or more silicone material wherein at least one of the silicone materials is curable or cross-linkable upon the application of the conditioner on the hair or during hair drying;
c) from about 70% to about 98% of an aqueous carrier.

13 Claims, No Drawings

(51) Int. Cl.
| | |
|---|---|
| *A61K 8/34* | (2006.01) |
| *A61K 8/36* | (2006.01) |
| *A61K 8/37* | (2006.01) |
| *A61K 8/44* | (2006.01) |
| *A61K 8/58* | (2006.01) |
| *A61K 8/19* | (2006.01) |
| *A61K 8/368* | (2006.01) |
| *A61K 8/42* | (2006.01) |
| *A61K 8/49* | (2006.01) |
| *A61K 8/81* | (2006.01) |
| *A61K 8/86* | (2006.01) |
| *A61Q 5/12* | (2006.01) |

(52) U.S. Cl.
CPC .............. *A61K 8/345* (2013.01); *A61K 8/361* (2013.01); *A61K 8/368* (2013.01); *A61K 8/37* (2013.01); *A61K 8/415* (2013.01); *A61K 8/416* (2013.01); *A61K 8/42* (2013.01); *A61K 8/44* (2013.01); *A61K 8/49* (2013.01); *A61K 8/585* (2013.01); *A61K 8/8111* (2013.01); *A61K 8/8158* (2013.01); *A61K 8/86* (2013.01); *A61Q 5/12* (2013.01)

(56) References Cited

U.S. PATENT DOCUMENTS

| | | | |
|---|---|---|---|
| 4,496,536 | A | 1/1985 | Moller et al. |
| 4,536,399 | A * | 8/1985 | Flynn ..................... A61K 8/26 424/69 |
| 4,678,475 | A | 7/1987 | Hoshowski et al. |
| 5,102,655 | A | 4/1992 | Yoshihara et al. |
| 5,384,114 | A | 1/1995 | Dowell et al. |
| 5,587,155 | A | 12/1996 | Ochiai et al. |
| 5,688,495 | A | 11/1997 | Rosen et al. |
| 6,001,340 | A | 12/1999 | Rosen et al. |
| 6,156,299 | A | 12/2000 | Rosen et al. |
| 6,294,186 | B1 | 9/2001 | Beerse et al. |
| 6,495,498 | B2 | 12/2002 | Niemiec et al. |
| 6,858,202 | B2 | 2/2005 | Niemiec et al. |
| 6,908,889 | B2 | 6/2005 | Niemiec et al. |
| 7,527,654 | B2 | 5/2009 | Plos |
| 8,512,686 | B2 | 8/2013 | Morioka |
| 8,968,712 | B2 | 3/2015 | Tanaka |
| 9,095,528 | B2 | 8/2015 | Desenne et al. |
| 9,216,146 | B2 | 12/2015 | Tanaka |
| 9,259,070 | B2 | 2/2016 | Fischer et al. |
| 9,265,321 | B2 | 2/2016 | Fischer et al. |
| 9,271,908 | B2 | 3/2016 | Allef et al. |
| 9,877,909 | B2 | 1/2018 | Cetti et al. |
| 10,111,815 | B2 | 10/2018 | Marsh et al. |
| 10,111,820 | B2 | 10/2018 | Marsh et al. |
| 10,117,819 | B2 | 11/2018 | Marsh et al. |
| 10,258,555 | B2 | 4/2019 | Punyani |
| 2002/0010228 | A1 | 1/2002 | Simendinger |
| 2003/0022936 | A1 | 1/2003 | Milbradt et al. |
| 2003/0143173 | A1 | 7/2003 | Buck |
| 2003/0170195 | A1 | 9/2003 | Houze et al. |
| 2003/0199584 | A1 | 10/2003 | Ahluwalia |
| 2003/0215405 | A1 | 11/2003 | Parker et al. |
| 2003/0223952 | A1 | 12/2003 | Wells et al. |
| 2004/0120911 | A1 | 6/2004 | Shah et al. |
| 2004/0180016 | A1 | 9/2004 | Buck |
| 2004/0251198 | A1 | 12/2004 | Lord |
| 2005/0136015 | A1 | 6/2005 | McKie et al. |
| 2005/0143268 | A1 | 6/2005 | Midha et al. |
| 2005/0169869 | A1 | 8/2005 | Laurent et al. |
| 2005/0175567 | A1 | 8/2005 | Khoshdel et al. |
| 2005/0196369 | A1 | 9/2005 | Ueyama et al. |
| 2005/0266034 | A1 | 12/2005 | Muller et al. |
| 2006/0078523 | A1 | 4/2006 | Vic |
| 2006/0165636 | A1 | 7/2006 | Hasebe et al. |
| 2006/0204466 | A1 | 9/2006 | Littau et al. |
| 2006/0286059 | A1 | 12/2006 | Yang et al. |
| 2007/0104667 | A1 | 5/2007 | Mondet et al. |
| 2007/0149423 | A1 | 6/2007 | Warr et al. |
| 2007/0261179 | A1 | 11/2007 | Dorkel et al. |
| 2008/0131389 | A1 | 6/2008 | Shibuya et al. |
| 2008/0138438 | A1 | 6/2008 | Taylor et al. |
| 2008/0194454 | A1 | 8/2008 | Morgan et al. |
| 2009/0169502 | A1 | 7/2009 | Quadir |
| 2009/0324531 | A1 | 12/2009 | Okada et al. |
| 2010/0297051 | A1 | 11/2010 | Feuillette |
| 2010/0300472 | A1 | 12/2010 | Malle et al. |
| 2010/0330007 | A1 | 12/2010 | Spindler et al. |
| 2011/0003016 | A1 | 1/2011 | Burry et al. |
| 2011/0226275 | A1 | 9/2011 | Fischer et al. |
| 2011/0256249 | A1 | 10/2011 | Campbell et al. |
| 2011/0269658 | A1 | 11/2011 | Dihora et al. |
| 2011/0274642 | A1 | 11/2011 | Yamaki et al. |
| 2012/0070398 | A1 | 3/2012 | Nagano et al. |
| 2012/0093751 | A1 | 4/2012 | Nagano et al. |
| 2012/0308506 | A1 | 12/2012 | Oku et al. |
| 2013/0064908 | A1 | 3/2013 | Noh |
| 2013/0125915 | A1 | 5/2013 | Nagase et al. |
| 2013/0164390 | A1 | 6/2013 | Richards et al. |

(56) References Cited

U.S. PATENT DOCUMENTS

| | | | |
|---|---|---|---|
| 2013/0167862 A1* | 7/2013 | Lopez | A61Q 5/08 132/208 |
| 2013/0259817 A1 | 10/2013 | Uehara et al. | |
| 2013/0259819 A1 | 10/2013 | Uehara et al. | |
| 2013/0306095 A1 | 11/2013 | Syed | |
| 2013/0309190 A1* | 11/2013 | Dimotakis | A61Q 5/06 424/70.17 |
| 2014/0079660 A1 | 3/2014 | Doi | |
| 2014/0154197 A1 | 6/2014 | Swaile et al. | |
| 2014/0179645 A1 | 6/2014 | Arndt | |
| 2014/0335042 A1* | 11/2014 | Peffly | A61K 8/342 424/70.121 |
| 2014/0349902 A1 | 11/2014 | Allef et al. | |
| 2015/0174052 A1 | 6/2015 | Mette et al. | |
| 2015/0313816 A1 | 11/2015 | Daubresse | |
| 2015/0313832 A1 | 11/2015 | Hilvert et al. | |
| 2015/0359716 A1 | 12/2015 | Marsh et al. | |
| 2015/0374609 A1 | 12/2015 | Cetti et al. | |
| 2016/0015608 A1 | 1/2016 | Marsh et al. | |
| 2016/0022558 A1 | 1/2016 | Kunin et al. | |
| 2016/0158128 A1 | 6/2016 | Marsh et al. | |
| 2016/0158135 A1 | 6/2016 | Marsh et al. | |
| 2016/0175209 A1 | 6/2016 | Walker et al. | |
| 2016/0228342 A1 | 8/2016 | Rose | |
| 2016/0287494 A1 | 10/2016 | Punyani et al. | |
| 2016/0287495 A1 | 10/2016 | Punyani et al. | |
| 2017/0157008 A1 | 6/2017 | Punyani et al. | |
| 2017/0157009 A1 | 6/2017 | Punyani et al. | |
| 2017/0157011 A1 | 6/2017 | Punyani et al. | |
| 2017/0216172 A1 | 8/2017 | Carballada et al. | |
| 2017/0281523 A1 | 10/2017 | Punyani et al. | |
| 2017/0290755 A1 | 10/2017 | Soh et al. | |
| 2018/0289603 A1 | 10/2018 | Punyani et al. | |
| 2018/0289605 A1 | 10/2018 | Punyani et al. | |

FOREIGN PATENT DOCUMENTS

| | | | |
|---|---|---|---|
| EP | 1674072 A1 | 6/2006 | |
| EP | 1787680 A2 | 5/2007 | |
| EP | 1326577 B1 | 10/2008 | |
| EP | 2036536 A1 | 3/2009 | |
| EP | 2392314 A1 | 12/2011 | |
| FR | 2931659 B1 | 3/2011 | |
| FR | 2968946 B1 | 4/2013 | |
| GB | 816750 | 7/1959 | |
| JP | S63156711 A | 6/1988 | |
| JP | H06256137 A | 9/1994 | |
| JP | 3009959 B2 | 2/2000 | |
| JP | 3026213 B2 | 3/2000 | |
| JP | 2001122737 A | 5/2001 | |
| JP | 2005145883 A | 6/2005 | |
| JP | 2005194261 A | 7/2005 | |
| JP | 3843051 B2 | 11/2006 | |
| JP | 2007070469 A | 3/2007 | |
| JP | 4329097 B2 | 9/2009 | |
| JP | 4452523 B2 | 4/2010 | |
| JP | 4625357 B2 | 2/2011 | |
| JP | 4679893 B2 | 5/2011 | |
| JP | 4883261 B2 | 2/2012 | |
| JP | 5086539 B2 | 11/2012 | |
| JP | 5228338 B2 | 7/2013 | |
| JP | 2014097931 A | 5/2014 | |
| JP | 5779399 B2 | 9/2015 | |
| WO | WO200128338 A2 | 4/2001 | |
| WO | WO200128339 A2 | 4/2001 | |
| WO | WO2011074134 A1 | 6/2011 | |
| WO | WO2012131848 A1 | 10/2012 | |
| WO | WO2014002668 A2 | 1/2014 | |
| WO | WO2014100970 A1 | 7/2014 | |
| WO | WO 2015/200778 A1 | 12/2015 | |

OTHER PUBLICATIONS

Naturally.com, "Salicylic Acid Shampoo for Curly Hair", pp. 1-3, 2011. (Year: 2011).*
PCT International Search Report and Written Opinion for PCT/US2017/024965 dated Jun. 13, 2017.
Dow Corning: "Leave-In Conditioner: Fast Dry", Dec. 9, 2015.
Dow Corning: "Revivel Hair Repair Cream: Ideal to Repair Heat Damaged Hair", Jan. 21, 2015.
Dow Corning: "Get on the FastTrack to Dry with silicones from Dow Corning", Nov. 19, 2015.
Dow Corning: "Rinse-Off Conditioner: Fast Dry", Dec. 9, 2015.
"De-Frizz Leave-In Treatment", Quality Collor Cosmeticos, May 1, 2014, Mintel.
"Infusion 23 (Colour) Ologie Leave-In Treatment", Procter & Gamble, Feb. 1, 2007, Mintel.
All Final and Non-Final Office Actions for U.S. Appl. No. 14/677,578, P&G Case 13769.
All Final and Non-Final Office Actions for U.S. Appl. No. 14/677,636, P&G Case 13770.
All Final and Non-Final Office Actions for U.S. Appl. No. 14/742,136, P&G Case 13355M.
All Final and Non-Final Office Actions for U.S. Appl. No. 14/742,145, P&G Case 13356M.
All Final and Non-Final Office Actions for U.S. Appl. No. 14/755,567, P&G Case 13461M.
All Final and Non-Final Office Actions for U.S. Appl. No. 14/959,234, P&G Case 13640M.
All Final and Non-Final Office Actions for U.S. Appl. No. 14/959,243, P&G Case 13641M.
All Final and Non-Final Office Actions for U.S. Appl. No. 15/093,075, P&G Case AA1008.
All Final and Non-Final Office Actions for U.S. Appl. No. 15/367,363, P&G Case 14117.
All Final and Non-Final Office Actions for U.S. Appl. No. 15/367,369, P&G Case 14118.
All Final and Non-Final Office Actions for U.S. Appl. No. 15/949,539, P&G Case 14768.
All Final and Non-Final Office Actions for U.S. Appl. No. 15/949,555, P&G Case 14769.
Anonymous: "Spotlight on Apricot Oil, Black Girl with Long Hair", Apr. 5, 2013, Retrieved from the internet: URL: http://blackgirllonghaircom/2013/04/spotlight-on-apricot-oil/, Retrieved Jun. 2, 2016.
John Frieda Frizzease conditioner product (John Frieda, Frizzease smooth start conditioner- https://www.johnfrieda.com/en-UK/products/frizz-ease/smooth-start-conditioner.html, last visit date: Jan. 17, 2018 (year 2018).
Khan, H., "5 ways to straighten your hair without heat", Hair Beauty Tips, Jul. 12, 2013, pp. 1-4.
Knothe et al., J. Am Oil Chem Soc., 86, pp. 843-856 (2009).
Medline Plus "Aging changes in hair and nails", US National Library of Medicine, Oct. 27, 2014, pp. 1-3.
Merriam-Webster Dictionary, obtained online at https://www.merriam-webster.com/dictionary/pH, downloaded on Jun. 29, 2018, pp. 1-14 (2018).
PCT International Search Report and Written Opinion for PCT/US2015/036192 dated Mar. 21, 2016.
PCT International Search Report and Written Opinion for PCT/US2015/036195 dated Dec. 16, 2015.
PCT International Search Report and Written Opinion for PCT/US2016/025827 dated Jun. 24, 2016.
PCT International Search Report and Written Opinion for PCT/US2016/064604 dated Apr. 10, 2017.
PCT International Search Report and Written Opinion for PCT/US2016/064606 dated Apr. 12, 2017.
PCT Invitation to Pay Additional Fees and, Where Applicable, Protest Fee for PCT/US2015/036192 dated Jan. 4, 2016.

(56) References Cited

OTHER PUBLICATIONS

PCT Invitation to Pay Additional Fees and, Where Applicable, Protest Fee for PCT/US2015/036195, dated Oct. 7, 2015.
PCT Invitation to Pay Additional Fees And, Where Applicable, Protest Fee for PCT/US2015/063888 dated Mar. 9, 2016.
PCT Invitation to Pay Additional Fees and, Where Applicable, Protest Fee for PCT/US2015/063893, dated Feb. 8, 2016.
PCT Invitation to Pay Additional Fees And, Where Applicable, Protest Fee for PCT/US2015/064608 dated Feb. 20, 2017, 9 pages.
PCT Invitation to Pay Additional Fees And, Where Applicable, Protest Fee for PCT/US2016/064604 dated Feb. 15, 2017, 10 pages.
PCT Invitation to Pay Additional Fees And, Where Applicable, Protest Fee for PCT/US2016/064606 dated Feb. 20, 2017, 14 pages.
Retrieved from internet: http://cosmetics.specialchem.com/inci/hydroxyethyl-urea, last visit May 10, 2017
Olivella, M., et al., "Salicylic acid permeation: A comparative study with different vehicles and membranes", Biocell, pp. 321-324 Year: 2006).
Benvenuti, http://www.futurederm.com/what-is-the-best-oil-for-your-hair-argan-oil-vs-pequi-oil-review/, 2011, downloaded Dec. 30, 2018.
LotionCrafter (https://lotioncrafter.com/reference/tech_data_lc995.pdf) available on archieve.org on Nov. 23, 2015, pp. 1-2 (2015).

* cited by examiner

COMPOSITION FOR FAST DRY OF HAIR

FIELD OF THE INVENTION

The present invention relates to a composition for providing a fast dry benefit on hair.

BACKGROUND OF THE INVENTION

After a shower, hair has primarily two types of water: a) capillary water and b) water penetrated inside hair. Water penetrated inside hair is further categorized into three types of water a) free water b) loosely bound water and c) bound water. To dry hair, it is important to remove capillary water and water inside hair. Currently technologies have been focusing on hydrophobic coatings to get rid of capillary water which sometimes results in greasy feel trade-off. The present invention is based on the finding that certain materials which can penetrate inside the hair and coat the hair surface can result in less amount of water on hair surface and inside the hair and result in less amount of energy required to remove water and in faster hair drying.

SUMMARY OF THE INVENTION

The present invention is directed to a hair conditioner composition comprising from about 0.15% to about 16% moisture control material or mixtures of moisture control materials wherein one or more moisture control material is selected from the group containing:
 i. Class I Moisture Control Material having the structure selected from:

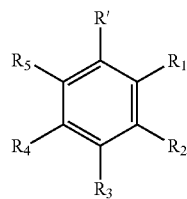

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;
 ii. Class IIa having the structure selected from:

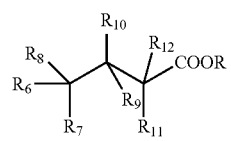

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;
 iii. Class IIb having the structure selected from:

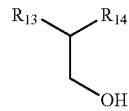

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;
 iv. Class IIc being an alcohol comprising an unsaturated double bond in the C2 position;
 v. Class IId being an alkyl-substituted glycol wherein the structure of such alkyl substituted glycol contains less than 20 carbon atoms;
 vi. Class IIe being a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;
 vii. Class IIf having a structure the structure selected from:

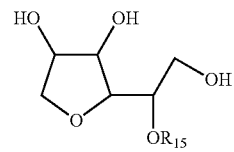

wherein $R_{15}$ could be hydrogen, alkyl, alkenyl, phenyl group and wherein the structure of the $R_{13}$ group contains less than 20 carbon atoms;
 viii. Class IIg being a fatty acid ester containing from 15-40 total carbon atoms; and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4;
 b) from about 0.1% to about 12% of one or more silicone material wherein at least one of the silicone materials is curable or cross-linkable upon the application of the conditioner on the hair or during hair drying;
 c) from about 70% to about 98% of an aqueous carrier.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions of the present invention can comprise, consist essentially of, or consist of the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit.

"Rinse-off" in reference to compositions, means compositions intended to be applied to keratinous substrate and subsequently removed by washing, rinsing or wiping within a few minutes or less from the application. These "rinse-off" compositions are to be distinguished from "leave-on" compositions, which are intended to be applied to and allowed to remain longer on the keratinous tissue.

"Leave-on," in reference to compositions, means compositions intended to be applied to and allowed to remain on the keratinous tissue. These leave-on compositions are to be distinguished from compositions, which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers. The leave-on compositions may be substantially free of cleansing or detersive surfactants. For example, "leave-on compositions" may be left on the keratinous tissue for at least 5 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography. "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

The mechanism of action for drying hair involves removal of capillary water and water inside hair. As after shower, hair has primarily two types of water a) capillary water and b) water penetrated inside hair. Water penetrated inside hair is further categorized into three types of water a) free water b) loosely bound water and c) bound water. To dry hair, it is important to remove capillary water and water inside hair. Currently technologies have been focusing on hydrophobic coatings to get rid of capillary water which sometimes results in greasy feel trade-off. Our invention is focusing on synergistically combining two types of materials so that the first type (Type I materials) can penetrate inside the hair and the second type (Type II materials) can modify the hair surface which results in less amount of water inside the hair and on hair surface. This method of treatment makes drying hair more readily achieved by requiring less amount of energy to remove water which results in drying the hair faster. Amount of absorption of water can be measured by using Dynamic Vapor Sorption (DVS) or Gravimetric method and amount of energy required to remove water can be measured by Differential Scanning Calorimetry (DSC).

In an embodiment of the present invention, materials include salicylic acid, 2,3-dihydroxybenzoic acid, 2,6-dihydroxybenzoic acid, 3-aminobenzoic acid, gallic acid, ethyl gallate, 5-chlorosalicylic acid, trans-ferulic acid, p-coumaric acid, ricinoleic acid, isovaleric acid, isobutyric acid, 2-hexyl-1-decanol, phytol and sorbitan caprylate. These materials are chosen from Molecular Class I and/or Molecular Class II or can also be used in combination to increase the size of the benefit.

In an embodiment of the present invention, the concentration of the Moisture Control Material or the concentration of the mixture of Moisture Control Material in a hair leave-on composition is from about 0.15% to about 16%, in an embodiment from about 0.2% to about 14%, in a further embodiment from about 1% to about 12%, and in yet a further embodiment from about 2% to about 10%.

Molecular Class I: Polar, Acidic Compounds with the Following Properties

Protein Binding (PB)>20 AND Molecular Volume (Mol. Vol).<500 AND log P<3 AND Hydrogen-binding (H-binding)>10 AND pKa<5.0, wherein PB is % protein binding, Mol. Vol is molecular volume (in $Å^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name (1% wt/vol) | PB | Mol. Vol. | log P | pKa | H-bond (Mpa^1/2) | % Reduction in amount of water absorbed |
|---|---|---|---|---|---|---|
| 2,4-Dihydroxybenzoic acid | 28 | 324 | 1.5 | 3.2 | 23 | 30 |
| 3-Hydroxybenzoic Acid | 38 | 314 | 1.6 | 4.3 | 20 | 20 |
| Gallic acid | 23 | 337 | 0.9 | 4.4 | 23 | 15 |
| 3-Aminobenzoic acid | 41 | 326 | 0.9 | 3.6 | 16 | 12 |
| 4-Aminobenzoic acid | 42 | 323 | 0.9 | 3.5 | 16 | 12 |
| 2,5-Dihydroxybenzoic acid | 31 | 329 | 1.6 | 2.9 | 23 | 27 |
| 3,4-Dihydroxybenzoic acid | 27 | 327 | 0.9 | 4.4 | 23 | 20 |
| 3,5-Dihydroxybenzoic acid | 27 | 327 | 0.9 | 4.1 | 23 | 15 |
| 2,6-Dihydroxybenzoic acid | 37 | 326 | 1.6 | 2.1 | 23 | 35 |
| 5-Chlorosalicylic acid | 56 | 361 | 2.3 | 3.0 | 21 | 28 |
| Salicylic acid | 44 | 320 | 2.1 | 3.1 | 20 | 18 |
| Trans-Ferulic Acid | 50 | 451 | 1.5 | 4.5 | 19 | 6 |
| p-Coumaric acid | 46 | 391 | 1.6 | 4.5 | 20 | 8.8 |
| 4-Hydroxybenzenesulphonic acid | 55 | 271 | 1.5 | 2.7 | 22 | 26 |
| 3-Chloro-4-hydroxybenzoic acid | 49 | 356 | 2.1 | 4.1 | 20 | 11 |
| 3,5-Dichloro-4-hydroxybenzoic acid | 51 | 397 | 2.8 | 3.8 | 20 | 15 |
| 2,5 Dihydroxyterephthalic acid | 20 | 375 | 1.1 | 2.1 | 22 | 18 |
| 3-Aminophenol | 45 | 284 | 0.6 | 4 | 17 | 14 |
| 3-Hydroxyanilinium chloride | 32 | 280 | 0.6 | 4 | 17 | 16 |
| 2-Aminophenol | 49 | 288 | 1.0 | 4 | 17 | 14 |
| 4-Aminophenol | 39 | 284 | 0.6 | 4 | 17 | 10 |
| N-4-Hydroxyphenylglycine | 37 | 388 | 1.3 | 3 | 13 | 15 | b) Molecular Class II:

Weakly polar to non-polar, weakly acidic to non-acidic compounds that have the following properties: PB>10 AND Mol. Vol.<1500 AND log P>0.5 AND pKa≥5 AND H-binding>4, wherein PB is % protein binding, Mol. Vol is molecular volume (in Å$^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name | PB | Mol. Vol. | logP | pKa | H-bond (MPa^1/2) | % reduction in water absorbed |
|---|---|---|---|---|---|---|
| 2-Hydroxyethyl salicylate | 45 | 419 | 1.5 | 8.3 | 19.1 | 10 |
| Ethyl gallate | 43 | 431 | 1.4 | 8.7 | 22.6 | 17 |
| Oleic Acid | 100 | 832 | 7 | 5 | 6.4 | 14 |
| Ricinoleic acid | 84 | 841 | 5.9 | 5 | 17.8 | 8.8 |
| Isovaleric acid | 29 | 295 | 1.3 | 5 | 9.7 | 15 |
| Isobutyric acid | 15 | 254 | 1 | 5 | 10.4 | 5 |
| 2-Hexyl-1-decanol | 87 | 745 | 6.8 | 15 | 10.1 | 11 |
| Phytol | 100 | 874 | 8.0 | 13 | 9.6 | 14 |
| Sorbitan caprylate | 32 | 695 | 1.3 | 12 | 21.8 | 11 |
| Glyceryl monooleate | 96 | 974 | 6.27 | 12.8 | 16.2 | 5 |
| Isostearyl isostearate | 100 | 1527 | 14.7 | 14 | 4.2 | 11 |
| Ethyl linoleate | 82 | 903 | 7.71 | 7.8 | 5.1 | 8 |
| Isopropyl myristate | 97 | 798 | 6.99 | 8.8 | 5.0 | 12 |
| Octyl salicylate | 82 | 646 | 5.4 | 7.1 | 11.7 | 14 |

A Class I having the structure selected from:

1) Class I having the structure selected from:

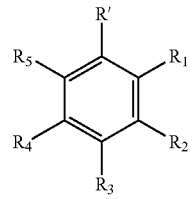

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;

2) Class II having the structure selected from:

A)

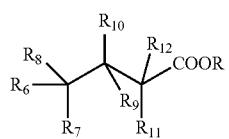

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;

B)

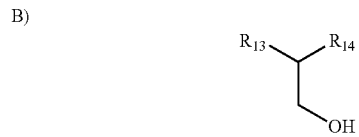

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;
 c) An alcohol comprising an unsaturated double bond in the C2 position. A non limiting example would be phytol.
 d) an alkyl-substituted glycol wherein the structure of such alkyl substituted glycol contains less than 20 carbon atoms;
 e) a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;

f)

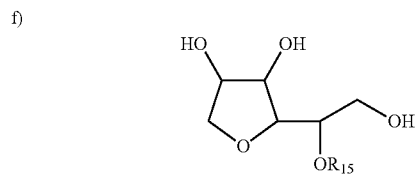

wherein $R_{15}$ could be hydrogen, alkyl, alkenyl, phenyl group and wherein the structure of the $R_{13}$ group contains less than 20 carbon atoms;
 g) a fatty acid ester containing from 15-40 total carbon atoms
and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4.

Curable/Cross-Linkable Silicones

Curable or cross-linkable silicones according to this invention that modify hair surface and synergestically reduce drying time of hair when used in the same composition with moisture control materials or when used in combination with moisture control materials but in separate compositions. Such curable or cross-linkable silicones are for drying hair faster. In an embodiment, curable or cross-linkable silicones are self cross-linkable amine functional silicones or a blend of functional silicones that will cross-link with each other on hair surface during drying. Such materials are usually added to rinse off treatment, rinse off conditioner or leave on treatment, but can also be added to shampoo. After depositing on hair surface such materials will cure or cross-linking to form higher molecular weight materials on hair surface, reducing amount of capillary water on hair surface and between hair fibers. In an embodiment, compositions of the present invention may contain a total of curable or cross-linkable silicones contain from about 0.1% to about 10%, in a further embodiment from about 0.5% to about 10% of the curable silicones, and in a further embodiment, from about 1% to about 5% and mixture thereof.

In a nonlimiting example, a curing reaction may be a condensation reaction between two silanol groups or between an amine and silanol group. The silanol-containing polymer can be a silicone resin. Commercially available self-curable or self-cross-linkable silicones include emulsion of Amodimethicone/Morpholinomethyl Silesquioxane Copolymer using Trideceth-5 and glycerin in water (Wacker Belsil ADM 8301 Eand ADM 6300E) or they include a blend of silicone materials such as Wacker ADM 8500, aminosilicone emulsion mentioned as amino methoxy functional polydimethylsiloxane (Dow Corning Silicone 531 and Silicone 536, Curable polymer that contains amine functional and dimethylpolysiloxane units (Momentive SF 1706), SWS E-210 (SWS Silicones Corp) are commercially available curable amine functional silicone blends that are useful for the present invention. Wacker ADM 8500, Dow Corning Silicone 531 and Silicone 536, Momentive SF 1706, SWS Silicones Corp. (SWS E-210) can be non-limiting examples of the group of curable amine functional silicones.

Useful curable or cross-linkable materials also include components of cross-linkable materials separately added to the fast dry composition without creating a blend of these materials first. Examples of such components of cross-linkable materials include Dow Corning AP-6087 and Momentive SR1000. Curing reaction may be a condensation reaction between two silanol groups or between an amine and silanol group.

In an embodiment of the present invention, the curable or crosslinkable silicone can be a silicone emulsion wherein the silicone emulsion comprises a crosslinked organopolysiloxane made from various reactive compounds, wherein each compound is comprised of one or more units represented by the following general formula:

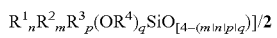

where
R$^1$ is morpholinomethyl having the structure:

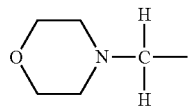

R$^2$ is
—(CH$_2$)$_3$—NH—(CH$_2$)$_2$NH$_2$
—(CH$_2$)$_3$—NH$_2$
R$^3$ is methyl
R$^4$ is hydrogen, methyl, ethyl or propyl
n is 0, 1, or 2
m is 0, 1, or 2
p is 0, 1, or 2
q is 0, 1, 2 or 3
n+m+p+q is less than or equal to 3
and wherein the crosslinked organopolysiloxane comprises on average at least one radical R$^1$ per molecule.

In the present invention, it has been surprisingly found that the curable silicones plus a suitable carrier to deposit an effective amount on hair are excellent for drying hair faster.

pH of Compositions

In an embodiment of the present invention, the table below demonstrates data of the difference in % reduction of amount of water absorbed from hair treated with leave on composition containing 1% salicylic acid in ethanol: water (50:50) at various values of pH vs control (hair treated with composition of ethanol:water (50:50). As shown in below table, at lower pH, the present invention demonstrates improved performance compared to higher pH.

|  | Formula Example | | | |
| --- | --- | --- | --- | --- |
| Raw Material | pH 3 | pH 4.2 | pH 7 | pH 10 |
| Distilled Water | QS | QS | QS | QS |
| Ethanol | 50.0 | 50.0 | 50.0 | 50.0 |
| Salicylic acid | 1.0 | 1.0 | 1.0 | 1.0 |
| Final pH | 3.2 | 4.2 | 7 | 10 |
| % Reduction of amount of water absorbed | 30 | 27 | 22 | 15 |

In an embodiment of the present invention, the pH of a composition of the present invention comprising material from Molecular Class I may be in the range of from about 1 to about 9, in another embodiment a pH of from about 2 to about 7, in a further embodiment a pH of from about 4 to about 5.5.

In an embodiment of the present invention, the Moisture control Material is a carboxylic acid ester. In an embodiment, the carboxylic acid ester is based on a fatty acid wherein the molecule of the fatty acid comprises of more than 14 carbon atoms. Non-limiting examples of such esters are isostearyl isostearate, methyl stearate, methyl palmitate, and methyl oleate. In another embodiment of the present invention, the carboxylic acid ester is part of a mixture of materials prepared via the reaction of natural oils using methanol. Non-limiting examples of such mixture is the mixture that is produced by the product of the reaction of refined palm kernel oil with methanol, followed by fractionation via distillation. A commercial product that meets this description is the Heavy Cut Ester CE-1875 (supplied by P&G Chemicals with CAS Number 6772-38-3) containing ingredients such as methyl stearate, methyl palmitate, methyl oleate as major ingredients, as well as methyl laurate, methyl myristate, methyl behenate and other materials as minor ingredients.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Formulation Examples to Evaluate the Effectiveness of Moisture Control Materials Leave-on Treatment Composition Preparation:

The leave-on treatment compositions are prepared by adding the Moisture Control Materials and perfume, if needed, into a 50:50 ethanol/water carrier and stirred until complete dissolution. The solution pH is adjusted using sodium hydroxide (50% w/w) to a final pH of 4.0-4.2. The Sepigel 305 is then added, if needed, and the solution is mixed using a high-speed-mixer for 2-5 minutes at 1800-2300 rpm until a uniform composition is obtained.

Leave-on Hair Treatment Protocol:

An amount of 0.20 g of each composition of Examples I to IV is spread via a syringe onto separate natural virgin brown hair switches weighing 2.0 g (dosage 0.10 g of solution per g of hair). The hair is allowed to air dry and then analyzed using the DVS method described above. The experiment is repeated for a dosage of 0.50 g of solution per g of hair. The hair in this case is also assessed by expert graders, as described below, in addition to the DVS analysis.

DVS Measurement:

An amount of 25-30 mg of hair with length of approximately 1 cm is weighed and hold for equilibration at 0% RH for 16 hours. After the 16-hour period, the RH is increased to 10% and maintained at this level for 6 hours. Then, the RH is increased by 10% after every 6 hours interval until it reaches 90% RH. The % reduction in amount of water absorbed is calculated as follows:

A=Amount of water absorbed by the hair treated with composition containing the Moisture Control Material B=Amount of water absorbed by the hair treated with control composition (only carrier) containing no Moisture Control Material $$\% \text{ reduction in amount of water absorbed} = [(B-A) \times 100]/B$$

Hair Switch Feel Assessment Method:

The treated hair switches are kept at high humidity (above 85% RH) for 2 hrs and then ten expert graders are asked to rate each of them in terms of tactile feel based on a 5 point scale, 5 being the highest (best feel) and 1 being the lowest rating.

Leave-on Treatment Formulation:

| Raw Material | Leave-on treatment Control (wt./wt.)% | I (wt./wt.)% | II (wt./wt.) % | III (wt./wt.) % | IV (wt./wt.) % | V (wt./wt.) % | VI (wt./wt.) % | VII (wt./wt.) % |
|---|---|---|---|---|---|---|---|---|
| Distilled Water | QS | QS | QS | QS | QS | QS | QS | QS |
| Ethanol | 50.00 | 50.00 | 50.00 | 50.00 | 50.00 | 50.00 | 50.00 | 50.00 |
| Polyacrylamide & C13-14 isoparaffin & Laureth-7 (Sepigel 305) | 1.85 | 1.85 | 1.85 | 1.85 | 1.85 | 1.85 | 1.85 | 1.85 |
| Perfume | 0.46 | 0.46 | 0.46 | 0.46 | 0.46 | 0.46 | 0.46 | 0.46 |
| Salicylic acid | 0 | 2.0 | 0 | 0 | 2.0 | 2.0 | 0.0 | 0.0 |
| 5-Chlorosalicylic acid | 0 | 0 | 2.0 | 0 | 0 | 0 | 2.0 | 2.0 |
| 2,4-Dihydroxybenzoic acid | 0 | 0 | 0 | 2.0 | 0.15 | 0.15 | 0.15 | 0.15 |
| Oleic acid | 0 | 0 | 0 | 0 | 0 | 0.25 | 0 | 0.25 |
| 2-Hexyl-1-decanol | 0 | 0 | 0 | 0 | 0 | 0.25 | 0 | 0.25 |
| Final pH | 4.2 | 4.2 | 4.2 | 4.2 | 4.2 | 4.2 | 4.2 | 4.2 |
| % Reduction in amount of water absorbed versus Leave-on Treatment Control at dose of 0.10 g of composition for 1.0 g of hair | — | — | — | — | 4 | 5 | 5 | 7 |
| % Reduction in amount of water absorbed versus Leave-on Treatment Control at dose of 0.50 g of composition for 1.0 g of hair. Control is dosed at 0.50 g of composition for 1.0 g of hair | — | 4 | 5 | 5 | 9 | 8 | 10 | 10 |
| Feel Rating Leave-on Treatment Control at dose of 0.10 g of composition for 1.0 g of hair | 1 | 1 | 2 | 2 | 2 | 3 | 2 | 4 |

| Raw Material | VIII | IX | X | XI | XII | XIII |
|---|---|---|---|---|---|---|
| Distilled Water | QS | QS | QS | QS | QS | QS |
| Ethanol | 50.0 | 50.0 | 50.0 | 50.0 | 50.0 | 50.0 |
| 5-Chlorosalicylic acid | 1.0 | | | 1.0 | 1.0 | 1.0 |
| 2-Hexyl-1-decanol | | | 5.0 | 5.0 | | 5.0 |
| Isostearyl isostearate | | 2.0 | | | 2.0 | 2.0 |
| Final pH | 4 | 4 | 4 | 4 | 4 | 4 |
| % reduction in amount of water absorbed versus Leave-on Treatment Control at dose of 0.10 g of composition for 1.0 g of hair | 1.3 | 0.7 | 1.0 | 2.0 | 1.4 | 3.0 |
| Feel Rating (on 5 scale point with 5 as highest and 1 as lowest) | 1 | 2 | 2 | 3 | 3 | 4 |

Results:

Formula I to XIII showed % reduction in amount of water absorbed. Higher % reduction in amount of water absorbed are observed in hair treated with higher doses of leave-on Formulas I-XIII.

The feel assessment results indicate that combinations of
(a) 5-Chlorosalicylic acid and 2-hexyl-1-decanol;
(b) 5-Chlorosalicylic acid and isostearyl isostearate;
(c) 5-Chlorosalicylic acid and 2-hexyl-1-decanol and isostearyl isostearate provide, not only water absorption reduction (resulting in fast hair drying benefit), but also tactile feel benefit. This is shown by the feel comparisons of (a) Example XI versus Examples VIII and IX, (b) Example XII versus Examples VIII and X, and (c) Example XIII versus Examples VIII, IX and X.

Rinse-Off Treatment Composition Preparation:

The rinse-off treatment compositions can be prepared by any conventional method well known in the art. The cationic surfactants and the fatty alcohols are mixed together and heated to from about 66° C. to about 85° C. to form an oil phase. Separately, the disodium EDTA, the Methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature.

Rinse-Off Hair Treatment Protocol:

All testing are performed on Caucasian Virgin hair switches weighing approximately 2.0 grams and having a length of approximately 6 inches. The hair switches are commercially available from IHIP (International Hair Importers). Three hair switches per rinse-off compositions per dosage are used. Each hair switch is washed with clarifying shampoo followed by a treatment with the rinse-off conditioner according to the following protocol.

An amount of 0.20 g of clarifying shampoo is spread via a syringe onto separate hair switch. That is, the dosage is 0.10 g of shampoo per g of hair. Each application consists of adding shampoo to the hair, milking for 30 seconds followed by rinsing for 30 seconds. Excess water is squeezed from the hair switches and then 0.1 g/g of the rinse off hair treatment is applied and milked for 30 seconds and left on hair to rest for 15 minutes and then rinsed off with water for 30 seconds.

OR

An amount of 0.20 g of clarifying shampoo is spread via a syringe onto separate hair switch. That is, the dosage is 0.10 g of shampoo per g of hair. Each application consists of adding shampoo to the hair, milking for 30 seconds followed by rinsing for 30 seconds. Excess water is squeezed from the hair switches and then 0.1 g/g of the rinse-off conditioner is applied and milked for 30 seconds and then rinsed for 30 seconds. This protocol is repeated for 5 times/cycles.

Leave-On Hair Treatment Protocol:

An amount of 0.20 g of clarifying shampoo is spread via a syringe onto separate hair switch. That is, the dosage is 0.10 g of shampoo per g of hair. Each application consists of adding shampoo to the hair, milking for 30 seconds followed by rinsing for 30 seconds. Excess water is squeezed from the hair switches and then 0.1 g/g of the leave on treatment is applied and milked for 30 seconds and left on hair for air dry at 40-50% RH at 25° C.-30° C.

Evaluation Methods

The hair switches that are treated with the rinse-off conditioner, deep conditioning treatment, leave on treatment compositions are evaluated using the following methodology.

a. Differential Scanning Calorimetry (DSC) Measurement

A DSC 204 Netzsch TASC 414/3A is used for the tests, which are performed in triplicate. The samples consist of approximately 5.5 mg of entire hair switches cut into pieces and homogenized. The sample is placed into T-Zero aluminum DSC pans, and then covered with stainless steel meshes. A sand baseline & burnoff is performed before running samples, and after every 10 samples. Measurements of ambient relative humidity are taken from a Dickson Logger in the room where analyses are performed. The tests are conducted within the temperature range of 5° C. to 300° C. at 5° C./minute under 200 ml/minute nitrogen purge. An empty pan of the same type is employed as a reference and tested under the same experimental conditions used for the samples. The standard error of this method ranges from 1 to 10%. Temperature measurements are taken at the endotherm peaks of water loss and degradation, an extrapolated onset is taken at the end of the water loss endotherm, and curve-fitting energy integration is performed for the entire endotherm.

b. Gravimetric Measurement

Hair Switches (4 g, 10 inches, Caucasian damaged wavy hair supplied by International Hair Importers) are weighed before the treatment in a weighing boat and are blow dried every minute and weighed simultaneously after treatment with different technologies. Blow dry settings such as temperature 37° C., with medium air speed flow and distance of 6 inches between blow drier and hair switches are kept constant throughout the experiment and between the treatments. Time at which there is no further drop in weight of hair switch is recorded as hair drying time.

TABLE 1

Rinse off Treatment Formulations

| | Formula | | | |
|---|---|---|---|---|
| | Ex. I (wt/wt) % | Ex. II (wt/wt) % | Ex. III (wt/wt) % | Ex. IV (wt/wt) % |
| BTMS/IPA[1] | 4.4 | 4.4 | 4.4 | 4.4 |
| Steareth-20[2] | 5.3 | 5.3 | 5.3 | 5.3 |
| Cetyl Alcohol[3] | 1.7 | 1.7 | 1.7 | 1.7 |
| Stearyl Alcohol[4] | 4.3 | 4.3 | 4.3 | 4.3 |
| Salicylic Acid[5] | 0.0 | 2.0 | 0.0 | 2.0 |
| Isostearyl Isostearate[6] | 0.0 | 1.0 | 0.0 | 1.0 |
| Amodimethicone[7] | 0.0 | 0.0 | 7.0 | 7.0 |
| 2-hexyl decanol[8] | 0.0 | 5.0 | 0.0 | 5.0 |
| Trimethylsiloxysilicate (MQ Resin)[9] | 0.0 | 0.0 | 0.007 | 0.007 |
| Amodimethicone/Morpholinomethyl Silsesquioxane Copolymer [10] | 0.0 | 0.0 | 2.5 | 2.5 |
| Silicone Quaternium-26 (PQAS)[11] | 2.5 | 2.5 | 0.0 | 0.0 |
| Disodium EDTA[12] | 0.1 | 0.1 | 0.1 | 0.1 |
| Methylchloroisothiazolinone (Kathon CG)[13] | 0.033 | 0.033 | 0.033 | 0.033 |
| Benzyl Alcohol[14] | 0.4 | 0.4 | 0.4 | 0.4 |
| NaOH | 0.6 | 0.6 | 0.6 | 0.6 |
| Perfume | 0.7 | 0.7 | 0.7 | 0.7 |
| Q.S. DI Water | 79.0 | 74.5 | 73.0 | 65.0 |
| Amount of Energy required to remove water (J/g) | 271 | 250 | 256 | 217 |
| Difference of Energy required to remove water (J/g) from control I | 0 | −21 | −15 | −54 |
| Time required to dry hair switch using blow drier (mins) | 12 | 7 | 6 | 4 |
| Standard deviation of amount of energy required to remove water | 4.4 | 2.8 | 16 | 10 |

[1]Supplied by Feixiang Chemicals (Zhangjingang) Co., Ltd.
[2]Supplied by Croda
[3]Supplied by P&G Chemicals
[4]Supplied by P&G Chemicals
[5]Supplied by API Corporation
[6]Crodamol ISIS supplied by Croda
[7]Amodimethicone supplied by Wacker
[8]Isofol 16 supplied by Sasol (Brunsbuettel, DE)
[9]Trimethylsiloxysilicate (MQ Resin) supplied by Wacker
[10] Amodimethicone/Morpholinomethyl Silsesquioxane Copolymer (20% active level) supplied by Wacker
[11]Silicone Quaternium-26 (PQAS) supplied by Momentive
[12]Trilon BD Powder supplied by BASF SE (Ludwigshafen, DE)
[13]Kathon CG supplied by Rohm & Haas Co (Philadelphia US)
[14]Supplied by Ineos Maastricht BV (Maastricht NL)

Results:

Above table 1 represents rinse-off conditioner compositions that are used for treating hair switches. As shown in the table, hair treated with these compositions require (a) different amount of energy to remove the water from hair and (b) different amount of time required to dry the hair switch. Hair treated with composition of Ex. IV, which contains moisture control material (MCM) and cross-linkable silicone shows the least amount of energy of 217 J/g (at 95% confidence interval) required to remove the water from hair compared to hair treated with Ex. II, which contains MCM and Ex. III, which contains cross-linkable silicone. The data indicate that, surprisingly, the reduction in energy required to dry hair switches treated with Ex. IV as compared to the energy required to dry hair switches treated with Control Ex. I (54 J/g) is larger than the added reductions in energy required to dry hair switches treated with Ex. II and Ex. III as compared to the same control Ex. I (36 J/g=15 J/g+21 J/g). This shows that there is an unexpected synergistic effect of the MCM and cross-linkable silicone ingredients in achieving dry hair.

Without being bound by theory, lower amount of energy and less time required to dry hair treated with MCM and cross-linkable silicone could be due to the penetration of Moisture Control Materials inside the hair fibers and the coating of the external hair surface by crosslinkable silicone. MCM can form stronger bonds with hair fibers than water and, as a result, reduce the strength of water-hair bonding interaction and the quantity of the water absorbed in the hair fiber. Similarly, the silicone on hair surfaces reduced the adsorption amount and/or the strength of interaction between water and hair. Alternatively, one may speculate that the interaction of hair and water becomes thermodynamically favorable in the presence of MCM and silicone because of the favorable entropic effect of less water being bound by the internal and external hair surface.

TABLE 2

Example of Gel Matrix containing Leave on Formula V comprising of both moisture control materials and cross-linkable silicone

|  | Formula Ex V (wt/wt) % |
|---|---|
| BTMS/IPA | 2.9619 |
| Steareth-200 | 1.3982 |
| Cetyl Alcohol | 1.1775 |
| Stearyl Alcohol | 2.8963 |
| Salicylic Acid | 0.2 |
| Isostearyl Isosterate | 1 |
| PPG-15 Stearyl Ether | 1 |
| Disodium EDTA | 0.127 |
| Kathon CG | 0.033 |
| Benzyl Alcohol | 0.4 |
| Perfume | 0.7 |
| Amodimethicone | 7.0 |

TABLE 2-continued

Example of Gel Matrix containing Leave on Formula V comprising of both moisture control materials and cross-linkable silicone

|  | Formula Ex V (wt/wt) % |
|---|---|
| Trimethylsiloxysilicate (MQ Resin) | 0.007 |
| Amodimethicone/Morpholinomethyl Silsesquioxane Copolymer | 2.5 |
| Q.S. DI Water | 78.5 |

TABLE 3

Example of Leave on Formula VI comprising of both moisture control materials and cross-linkable silicone

| Raw Material | Formula Example Ex VI (wt./wt.) % |
|---|---|
| Distilled Water | QS |
| Polyacrylamide & C13-14 Isoparaffin & Laureth-7 (Sepigel 305) | 1.85 |
| Salicylic acid | 2 |
| Isostearyl Isostearate | 2 |
| 2-Hexyl-1-decanol | 5 |
| Amodimethicone | 7.0 |
| Trimethylsiloxysilicate (MQ Resin) | 0.007 |
| Amodimethicone/Morpholinomethyl Silsesquioxane Copolymer | 2.5 |

Regimen:

In another embodiment of the present invention, the beneficial reduction in energy and time required for drying hair is achieved by hair treatment regimen comprising a shampoo composition containing MCM followed by treating the hair with rinse-off or leave-on composition containing cross-linkable silicone or mixture of more than one such silicones. Alternatively, the regimen can comprise both rinse-off and leave-on treatments with rinse-off and leave-on conditioner compositions wherein at least one or both compositions contain at least one cross-linkable silicone.

TABLE 1

Regimen Examples at each step may contain 1 or more of moisture control materials, curable silicone, functional silicone and durable silicone

| Regimen Steps | Regimen Example 1 | Regimen Example 2 | Regimen Example 3 | Regimen Example 4 | Regimen Example 5 | Regimen Example 6 |
|---|---|---|---|---|---|---|
| Step 1 | Shampoo | Deep Conditioning Treatment*/ Soaking# | Shampoo | Shampoo | Shampoo | Shampoo |
| Step 2 | Deep conditioning Treatment*/ Soaking# | Shampoo | Deep Conditioning Treatment*/ Soaking# | Conditioner | Deep Conditioning Treatment*/ Soaking# | Leave-on |
| Step 3 | Conditioner | Conditioner | Leave-on | Leave-on |  |  |
| Step 4 | Leave-on | Leave-on |  |  |  |  |

*Deep Conditioning Treatment Time (T) and Dosage (D) may vary from regimen to regimen
Soaking Time may vary from regimen to regimen Conditioner Treatment Composition Having a Gel Matrix The conditioner composition may comprise a gel matrix comprising (1) one or more high melting point fatty compounds, (2) a cationic surfactant system, and (3) an aqueous carrier.

A. Cationic Surfactant System

The gel matrix of the conditioner composition includes a cationic surfactant system. The cationic surfactant system can be one cationic surfactant or a mixture of two or more cationic surfactants. Preferably, the cationic surfactant is selected from mono-long alkyl quaternized ammonium salt, di-long alkyl quaternized ammonium salt, mono-long alkyl amidoamine salt or mixtures thereof. The cationic surfactant system can be included in the composition at a level by weight of from about 0.1% to about 10%, from about 0.5% to about 8%, from about 0.8% to about 5%, and from about 1.0% to about 4%.

The mono-long alkyl quaternized ammonium salt cationic surfactants useful herein are those having one long alkyl chain which has from about 12 to about 30 carbon atoms, preferably from 16 to 24 carbon atoms, more preferably 18 to 22 carbon atoms. The remaining groups attached to the nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms. The counterion is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Nonlimiting examples of such mono-long alkyl quaternized ammonium salt cationic surfactants include: behenyl trimethyl ammonium salt.

The di-long alkyl quaternized ammonium salt cationic surfactants useful herein are those having two long alkyl chains of from 12 to 30 carbon atoms, more preferably from 16 to 24 carbon atoms, still more preferably from 16 to 22 carbon atoms or an aromatic, alkoxy, polyoxyalkylene, alkylamido, hydroxyalkyl, aryl or alkylaryl group having up to about 30 carbon atoms. The remaining substituents on the nitrogen atom are selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms. The counterion is a salt forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Nonlimiting examples of di-long alkyl cationic surfactants include dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

High Melting Point Fatty Compound

The high melting point fatty compound can be included in the composition at a level of from about 0.5%, preferably from about 1.0%, more preferably form about 1.5%, still more preferably from about 2%, even more preferably from about 4%, and to about 15%, preferably to about 10% by weight of the composition, in view of providing the benefits of the present invention. The high melting point fatty compound useful herein have a melting point of 25° C. or higher, preferably 40° C. or higher, more preferably 45° C. or higher, still more preferably 50° C. or higher. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

Aqueous Carrier The conditioner gel matrix of the leave-on treatment composition includes an aqueous carrier which can be water or a mixture of water and water-miscible solvents.

Rheology Modifier

In one embodiment, the leave-on hair care composition comprises a rheology modifier to increase the substantivity and stability of the composition. Any suitable rheology modifier can be used. In an embodiment, the leave-on hair care composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In one embodiment, the leave-on hair care composition may comprise rheology modifiers that are homopolymers based on acrylic acid, methacrylic acid or other related derivatives, non-limiting examples include polyacrylate, polymethacrylate, polyethylacrylate, and polyacrylamide.

In another embodiment, the rheology modifiers may be alkali swellable and hydrophobically-modified alkali swellable acrylic copolymers or methacrylate copolymers non-limiting examples include acrylic acid/acrylonitrogen copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylateskinylneodecanoate crosspolymer, and acrylates/C10-C30 alkyl acrylate crosspolymer.

In a further embodiment, the rheology modifiers may be crosslinked acrylic polymers, a non-limiting example includes carbomers.

In a father embodiment, the rheology modifiers may be alginic acid-based materials; non-limiting examples include sodium alginate, and alginic acid propylene glycol esters.

In a further embodiment, the rheology modifier may be an associative polymeric thickeners, non-limiting examples include: Hydrophobically modified cellulose derivatives; Hydrophobically modified alkoxylated urethane polymers, nonlimiting example include PEG-150/decyl alcohol/SMDI copolymer, PEG-150/stearyl alcohol/SMDI copolymer, polyurethane-39; Hydrophobically modified, alkali swellable emulsions, non-limiting examples include hydrophobically modified polyacrylates, hydrophobically modified polyacrylic acids, and hydrophobically modified polyacrylamides; hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, in another embodiment from 30-200, in a further embodiment from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

In a further embodiment, the rheology modifier may be cellulose and derivatives; nonlimiting examples include microcrystalline cellulose, carboxymethylcelluloses, hydroxyethylcellulose, hydroxypropylcellulose, hydroxypropylmethylcellulose, methylcellulose, ethylcellulose, nitro cellulose, cellulose sulfate, cellulose powder, and hydrophobically modified celluloses.

In an embodiment, the rheology modifier may be a guar and guar derivatives; nonlimiting examples include hydroxypropyl guar, and hydroxypropyl guar hydroxypropyl trimonium chloride.

In an embodiment, the rheology modifier may be polyethylene oxide, polypropylene oxide, and POE-PPO copolymers.

In an embodiment, the rheology modifier may be polyvinylpyrrolidone, crosslinked polyvinylpyrrolidone and derivatives. In a further embodiment, the rheology modifier may be polyvinyalcohol and derivatives.

In a further embodiment, the rheology modifier may be polyethyleneimine and derivatives.

In another embodiment, the rheology modifier may be silicas; nonlimiting examples include fumed silica, precipitated silica, and silicone-surface treated silica.

In an embodiment, the rheology modifier may be waterswellable clays non-limiting examples include laponite, bentolite, montmorilonite, smectite, and hectonite.

In an embodiment, the rheology modifier may be gums nonlimiting examples include xanthan gum, guar gum, hydroxypropyl guar gum, Arabia gum, tragacanth, galactan, carob gum, karaya gum, and locust bean gum.

In a further embodiment, the rheology modifier may be, dibenzylidene sorbitol, karaggenan, pectin, agar, quince seed (Cydonia oblonga Mill), starch (from rice, corn, potato, wheat, etc), starch-derivatives (e.g. carboxymethyl starch, methylhydroxypropyl starch), algae extracts, dextran, succinoglucan, and pulleran, Non-limiting examples of rheology modifiers include acrylamide/ammonium acrylate copolymer (and)polyisobutene (and) polysorbate 20, acrylamide/sodium acryloyldimethyl taurate copolymer/isohexadecane/polysorbate 80, acrylates copolymer; acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC), carbomer, crosslinked polyvinylpyrrolidone (PVP), dibenzylidene sorbitol, hydroxyethyl ethylcellulose (EHEC), hydroxypropyl methylcellulose (HPMC), hydroxypropyl methylcellulose (HPMC), hydroxypropylcellulose (HPC), methylcellulose (MC), methylhydroxyethyl cellulose (MEHEC), PEG-150/deC yl alcohol/SMDI copolymer, PEG-150/stearyl alcohol/SMDI copolymer, polyacrylamide/C13-14 isoparaffin/laureth-7; polyacrylate 13/polyisobutene/polysorbate 20; polyacrylate crosspolymer-6, polyamide-3; polyquaternium-37 (and) hydrogenated polydecene (and) trideceth-6, polyurethane-39, sodium acrylate/acryloyldimethyltaurate/dimethylacrylamide, crosspolymer (and) isohexadecane (and) polysorbate 60; sodium polyacrylate. Exemplary commercially-available rheology modifiers include ACULYN™ 28, Klucel M CS, Klucel H CS, Klucel G CS, SYLVACLEAR AF1900V, SYLVACLEAR PA1200V, Benecel E10M, Benecel K35M, Optasense RMC70, ACULYN™ 33, ACULYN™ 46, ACULYN™ 22, ACULYN™44, Carbopol Ultrez 20, Carbopol Ultrez 21, Carbopol Ultrez 10, Carbopol Ulterez 30, Carbopol 1342, Sepigel™ 305, Simulgel™ 600, Sepimax Zen, and combinations thereof.

Carrier

According to another aspect of the present invention, the leave-on hair care compositions may further include at least about 20 weight percent of an aqueous carrier. According to one embodiment, the aqueous carrier may be prepared from demineralized or distilled water, for example. In an embodiment of the present invention, the carrier may comprise water, organic solvents (miscible or non-miscible with water), silicone solvents or a mixture thereof. In one embodiment of the present invention, a volatile carrier may include water or a mixture of water and organic solvents. In a further embodiment, the solvents may be dermatologically acceptable.

In a further embodiment, the carrier may comprise water with minimal or no significant concentrations of organic solvent, except as otherwise incidentally incorporated into the composition as minor ingredients of other components. In another embodiment, water, organic and silicone solvents that have boiling points below or equal to 250° C. may be volatile solvents and volatile carriers. In one embodiment, solvents with boiling points above 250° C. may be considered non-volatile.

Non-limiting examples of a carrier may include water and solutions or mixtures of water with lower alkyl alcohols and/or polyhydric alcohols. Examples of lower alkyl alcohols are monohydric alcohols having 1 to 6 carbons such as ethanol, methanol, propanol, isopropanol, butanol, pentanol, and hexanol. Examples of polyhydric alcohols are glycols, such as dipropylene glycol, propylene glycol, butylene glycol, 1,4-butanediol, 3-allyloxy-1,2-propanediol, 1,2-hexanediol, 1,6-hexanediol, 1,3-butanediol, 1,3-propanediol, 2,2'-thiodiethanol, glycerin and other diols.

Other non-limiting examples of organic solvents include polyglycols such as polypropylene glycol, polyethylene glycol, mixture of butylene glycol, polypropylene glycol, polyethylene glycol and ethers, such as dipropylene glycol n-butyl ether, sugars, and sugar derivatives.

Penetration of Moisture Control Material Inside the Hair

In an embodiment of the present invention, compositions can comprise of glycols, polyglycols, urea, ethers or mixture thereof. These materials increase penetration of moisture control actives such as salicylic acid, 5-chloro salicylic acid, improving their performance Propylene glycol, butylene glycol and other glycols, increase penetration of 5-chlorosalicylic acid inside hair as it acts as carrier for the actives to penetrate further. As active penetration increases, there is an increase in efficacy of the active, i.e. there is increase in % reduction of amount of water absorbed as shown below in Table 5. Table 5 shows the amount of 5-chlorosalicylic acid that penetrates inside oxidatively damaged hair after hair treatment with two different compositions. It also shows the % reduction in amount of water absorbed observed after the treatment versus treatment with control compositions. These results demonstrate that 5-chlorosalicylic acid penetrates 4 times more in the presence of propylene glycol and there is an increase in % reduction of amount of water absorbed as measured by DVS of approximate 4 times more than without propylene glycol. A further non-limiting example of a material that enhances the penetration of moisture control material is 2-hydroxyethyl urea. Leave on treatment compositions that contain 2% of 2-hydroxyethyl urea increases the penetration of salicylic acid inside hair by 14% compared to the corresponding composition that does not contain 2-hydroxyethyl urea (see example XXVII and XXVIII).

TABLE 5

Enhancing of hair penetration of Moisture Control Material in oxidatively damaged (bleached) Caucasian hair

| | Formula Example | | | | |
|---|---|---|---|---|---|
| Raw Material | Control | XXV | XXVI | XXVII | XXVIII |
| Distilled Water | 50.0% | 48.93% | 43.9% | 48.93% | 48.00% |
| Ethanol | 50.0% | 48.93% | 43.9% | 48.93% | 48.00% |
| 5-Chlorosalicylic acid | 0.0% | 2.0% | 2.0% | 0.0% | 0.0% |
| 2-hydroxyethyl urea | 0.0% | 0.0% | 0.0% | 0.0% | 2.0% |
| Salicylic acid | 0.0% | 0.0% | 0.0% | 2.0% | 2.0% |
| 2,4-Dihydroxy-benzoic acid | 0.0% | 0.15% | 0.15% | 0.0% | 0.0% |
| Propylene glycol | 0.0% | 0% | 10% | 0% | 0.0% |
| Composition pH adjusted to | 4.2 | 4.2 | 4.2 | 4.2 | 4.2 |
| % Reduction in amount of water absorbed versus control treatment | — | 0.67% | 3% | — | — |
| Amount of 5-chlorosalicylic acid inside the hair (mg/g of hair) | — | 1 | 3.97 | — | — |
| Amount of Salicylic acid inside hair (mg/g of hair) after 5 cycles | — | — | — | 4.7 | 5.6 |

The penetration amount of 5-chlorosalicylic acid is determined using the following protocol. Each hair tress is extracted 3 times with 0.1% TFA (Trifluoroacetic acid) in methanol and the individual extracts are analyzed separately using HPLC method.

In addition to the increase of the penetration amount of the moisture control material, the presence of glycol in the composition prevents the crystallization of part of the moisture control material in the surface of the hair. Such crystallization causes a non-smooth, negative hair feel, which may be perceived by consumers as hair damage or lack of conditioning.

It has been observed that in an embodiment of the present invention the presence of propylene glycol may provide penetration enhancement for Molecular Class I and Class II materials.

Increase in the penetration amount of the moisture control material results in increase in % reduction in amount of water absorbed, further leading to faster hair drying because of less amount of water present in the hair.

Silicones

The conditioning agent of the compositions of the present invention can be a silicone conditioning agent. The silicone conditioning agent may comprise volatile silicone, non-volatile silicone, or combinations thereof. The concentration of the silicone conditioning agent typically ranges from about 0.01% to about 10%, by weight of the composition, from about 0.1% to about 8%, from about 0.1% to about 5%, and/or from about 0.2% to about 3%. Non-limiting examples of suitable silicone conditioning agents, and optional suspending agents for the silicone, are described in U.S. Reissue Pat. No. 34,584, U.S. Pat. Nos. 5,104,646, and 5,106,609, which descriptions are incorporated herein by reference. The silicone conditioning agents for use in the compositions of the present invention can have a viscosity, as measured at 25° C., from about 20 to about 2,000,000 centistokes ("csk"), from about 1,000 to about 1,800,000 csk, from about 50,000 to about 1,500,000 csk, and/or from about 100,000 to about 1,500,000 csk.

The dispersed silicone conditioning agent particles typically have a volume average particle diameter ranging from about 0.01 micrometer to about 50 micrometer. For small particle application to hair, the volume average particle diameters typically range from about 0.01 micrometer to about 4 micrometer, from about 0.01 micrometer to about 2 micrometer, from about 0.01 micrometer to about 0.5 micrometer. For larger particle application to hair, the volume average particle diameters typically range from about 5 micrometer to about 125 micrometer, from about 10 micrometer to about 90 micrometer, from about 15 micrometer to about 70 micrometer, and/or from about 20 micrometer to about 50 micrometer.

Additional material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989), incorporated herein by reference.

Silicone emulsions suitable for use in the embodiments of the present invention include, but are not limited to, emulsions of insoluble polysiloxanes prepared in accordance with the descriptions provided in U.S. Pat. No. 4,476,282 and U.S. Patent Application Publication No. 2007/0276087. Accordingly, suitable insoluble polysiloxanes include polysiloxanes such as alpha, omega hydroxy-terminated polysiloxanes or alpha, omega alkoxy-terminated polysiloxanes having a molecular weight within the range from about 50,000 to about 500,000 g/mol. The insoluble polysiloxane can have an average molecular weight within the range from about 50,000 to about 500,000 g/mol. For example, the insoluble polysiloxane may have an average molecular weight within the range from about 60,000 to about 400,000; from about 75,000 to about 300,000; from about 100,000 to about 200,000; or the average molecular weight may be about 150,000 g/mol. The insoluble polysiloxane can have an average particle size within the range from about 30 nm to about 10 micron. The average particle size may be within the range from about 40 nm to about 5 micron, from about 50 nm to about 1 micron, from about 75 nm to about 500 nm, or about 100 nm, for example.

The average molecular weight of the insoluble polysiloxane, the viscosity of the silicone emulsion, and the size of the particle comprising the insoluble polysiloxane are determined by methods commonly used by those skilled in the art, such as the methods disclosed in Smith, A. L. *The Analytical Chemistry of Silicones*, John Wiley & Sons, Inc.: New York, 1991. For example, the viscosity of the silicone emulsion can be measured at 30° C. with a Brookfield viscometer with spindle 6 at 2.5 rpm. The silicone emulsion may further include an additional emulsifier together with the anionic surfactant, Other classes of silicones suitable for use in compositions of the present invention include but are not limited to: i) silicone fluids, including but not limited to, silicone oils, which are flowable materials having viscosity less than about 1,000,000 csk as measured at 25° C.; ii) aminosilicones, which contain at least one primary, secondary or tertiary amine; iii) cationic silicones, which contain at least one quaternary ammonium functional group; iv) silicone gums; which include materials having viscosity greater or equal to 1,000,000 csk as measured at 25° C.; v) silicone resins, which include highly cross-linked polymeric siloxane systems; vi) high refractive index silicones, having refractive index of at least 1.46, and vii) mixtures thereof.

Organic Conditioning Materials

The conditioning agent of the compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Hair Health Actives

In an embodiment of the present invention, a scalp health active may be added to provide scalp benefits. This group of materials is varied and provides a wide range of benefits including anti-dandruff, anti-fungal, anti-microbial, moisturization, barrier improvement, and anti-oxidant, anti-itch, and sensates. Such skin health actives and scalp care actives include but are not limited to: zinc pyrithione, climbazole, octopirox, selenium sulfide, vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, isocyclomone, benzyl alcohol, and natural extracts/oils including peppermint, spearmint, argan, jojoba and aloe.

Anti-Dandruff Actives

In an embodiment of the present invention, the compositions may contain anti-dandruff agents. When present in these compositions, the anti-dandruff agent is typically included in an amount of about 0.01 wt. % to about 5 wt. %, based on the total weight of the personal care composition. In these compositions, the anti-dandruff particulate should be physically and chemically compatible with other ingredients of the composition, and should not otherwise unduly impair product stability, aesthetics, or performance Anti-dandruff agents suitable for use in personal care compositions include pyridinethione salts, azoles (e.g., ketoconazole, econazole, climbazole and elubiol), selenium sulfide, particulate sulfur, salicylic acid, and mixtures thereof. A typical anti-dandruff agent is pyridinethione salt. Personal care compositions can also include a zinc-containing layered material. An example of a zinc-containing layered material can include zinc carbonate materials.

Of these, zinc carbonate and pyridinethione salts (particularly zinc pyridinethione or "ZPT) are common in the composition, and often present together.

In addition to the anti-dandruff active, compositions may also include one or more anti-fungal or anti-microbial actives in addition to the metal pyrithione salt actives. Suitable anti-microbial actives include coal tar, sulfur, charcoal, whitfield's ointment, castellani's paint, aluminum chloride, gentian violet, octopirox (piroctone olamine), ciclopirox olamine, undecylenic acid and it's metal salts, US 2011/0305778 A1 Dec. 15, 2011 potassium permanganate, selenium sulphide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone and azoles, and combinations thereof. Typical anti-microbials include itraconazole, ketoconazole, selenium sulphide and coal tar.

Optional Ingredients

The compositions of the present invention can also additionally comprise any suitable optional ingredients as desired. For example, the composition can optionally include other active or inactive ingredients.

The compositions may include other common hair ingredients such as other anti-dandruff actives, minoxidil, conditioning agents, and other suitable materials. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, rheology modifiers, hair conditioning agents, and surfactants.

The formulations of the present invention may be present in typical hair care compositions. They may be in the form of solutions, dispersion, emulsions, powders, talcs, encapsulated, spheres, spongers, solid dosage forms, foams, and other delivery mechanisms. The composition of the present invention may be hair tonics, leave-on hair products such as conditioners, treatment, and styling products, and any other form that may be applied to the hair.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the hair care composition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of Embodiments of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair conditioner composition comprising:
   a) from about 0.15% to about 16% of at least two moisture control materials wherein the at least two moisture control materials are selected from the group consisting of:
      i. Class I Moisture Control Material having the structure selected from:

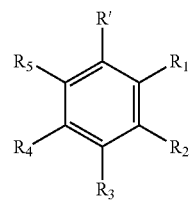

wherein R' is —COOY, sulfonic acid, or —C═CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH═CH—COOR, and wherein the moisture control material is an acidic material and further wherein the moisture control material has a % protein binding higher than 20 and molecular volume lower than 500 and partition coefficient octanol to water (log P) lower than 3 and hydrogen binding higher than 1 and pKa lower than 5.0;
      ii. Class IIa having the structure selected from;

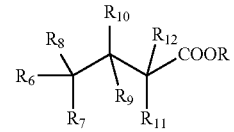

wherein R is hydrogen or metal ion, R is methyl, ethyl, propyl, alkenyl or phenyl having less than 12 carbon atoms and wherein $R_7$, $R_8$, $R_9$, $R_{10}$, $R_{12}$ are hydrogen, methyl, ethyl, propyl, phenyl, hydroxyl, methoxy or ethoxy groups; and
      iii. Class IIb having the structure selected from:

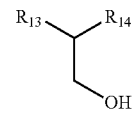

an alcohol wherein $R_{13}$ is an alkyl, alkenyl, straight or branched carbon chains and; and wherein $R_{14}$ is hydrogen, hydroxyl, alkyl, methyl, ethyl and propyl wherein the structure of such alcohol contains less than 20 total carbon atoms;
wherein the at least two moisture control materials comprise a combination of salicylic acid and isostearyl isostearate, a combination of salicylic acid and 2-hexyl decanol, and mixtures thereof;
wherein the moisture control material of Class IIs weakly to non-acidic and further wherein the moisture control material of Class II has protein binding higher than 10 and molecular volume lower than 1500 and log P higher than 0.5 and pKa of 5 or higher and hydrogen-binding higher than 4;
   b) from about 0.1% to about 12% of at least one amine functional silicone material wherein the at least one of the silicone materials is curable or cross-linkable upon the application of the conditioner on the hair or during haft drying; wherein the curable amine functional silicone is a sell-curable or self-cross-linkable silicone selected from the group consisting of emulsion of amodimethicone/morpholinomethyl silsesquioxane copolymer, aminosilicone emulsions as amino methoxy functional polydimethylsiloxane, and mixtures thereof;
   c) from about 70% to about 98% of an aqueous carrier.

2. A hair composition according to claim 1 wherein hair treated with the composition requires 20% less energy to dry compared to hair treated a composition which does not comprise the moisture control materials and the curable or cross-linkable amino functional silicone of claim 1.

3. A hair conditioner composition according to claim 1 wherein the amine functional silicone material is self cross-linkable amine functional silicones.

4. A hair conditioner composition according to claim 1 wherein the amine functional silicone material is selected from the group consisting of self-curable or self-cross-linkable silicones and mixtures thereof.

5. A hair conditioner composition according to claim 1 wherein the amine functional silicone material is curable or cross-linkable and is a curable amine functional silicone.

6. A composition according to claim 4 wherein the amine functional silicone material is a blend of silicones of emulsion of amodimethicone/morpholinomethyl silsesquioxane copolymer and aminosilicone emulsions as amino methoxy functional polydimethylsiloxane.

7. A hair conditioner composition according to claim 1 wherein the ingredient (a) is from about 0.2% to about 14%.

8. A hair conditioner composition according to claim 1 wherein the ingredient (a) material is from about 1% to about 12%.

9. A method of treating hair using the hair conditioner composition of claim 1 comprising the steps:
   a. applying the hair conditioner composition on wet or dry hair; and
   b. spreading the hair conditioner composition on hair fibers,
   wherein hair treated with the composition requires 20% less energy to dry compared to hair treated with a composition which does not comprise the moisture control materials and the curable or cross-linkable amino functional silicone of claim 1.

10. A method of treating hair using a regimen of at least two hair conditioner compositions comprising the steps:
    a. applying a first conditioner composition on wet or dry hair comprising:
       (1) from about 0.15% to about 16% of at least two moisture control materials wherein the at least two moisture control materials are selected from the group consisting of:
          i. Class 1 Moisture Control Material having the structure selected from:

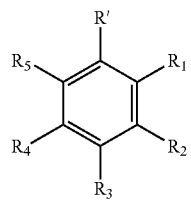

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sultanate, nitro, or —CH=CH—COOR, and wherein the moisture control material is an acidic material and further wherein the moisture control material has a % protein binding higher than 20 and molecular volume lower than 500 and partition coefficient octanol to water (log P) lower than 3 and hydrogen binding higher than 10 and pKa lower than 5.0;
          ii. Class IIa having the structure selected from:

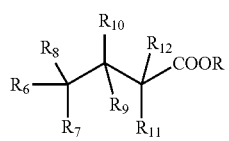

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups; and
          iii. Class IIb having the structure selected from:

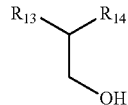

an alcohol wherein $R_{13}$ is an alkyl, alkenyl, straight or branched carbon chains and; and wherein $R_{14}$ is hydrogen, hydroxyl, alkyl, methyl, ethyl and propyl wherein the structure of such alcohol contains less than 20 total carbon atoms;
   wherein the at least two moisture control materials comprise a combination of salicylic acid and isostearyl isostearate, a combination of salicylic acid and 2-hexyl decanol, and mixtures thereof; and
   wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4;
       (2) from about 70% to about 98% of an aqueous carrier,
    b. spreading the first conditioner composition on hair fibers;
    c. applying a second conditioner composition on wet or dry hair comprising:
       (1) from about 0.1% to about 12% of at least one amine functional silicone material wherein the at least one of the silicone materials is curable or cross-linkable upon the application of the conditioner on the hair or during hair drying; wherein the curable amine functional silicone is a self-curable or self-cross-linkable silicone selected from the group consisting of emulsion of amodimethicone/morpholinomethyl silsesquioxane copolymer, aminosilicone emulsions as amino methoxy functional polydimethylsiloxane, and mixtures thereof;
       (2) from about 70% to about 98% of an aqueous carrier;
    wherein hair treated with the regimen requires 20% less energy to dry compared to hair treated with a corresponding regimen with the compositions which do not comprise the said moisture control materials and the said curable or cross-linkable amino functional silicone,
    d. spreading the composition on hair fibers.

11. A hair conditioner composition according to claim 1 wherein the composition further comprises materials selected from the group consisting of conditioning materials, solvents, rheology modifier, thickeners, hair health actives, anti-dandruff actives, anti-oxidants, pigments, abrasives, absorbents, biological actives, buffering agents, chelating agents, opacifying agents, pH adjusters and mixtures thereof.

12. A hair conditioner composition according to claim 1 wherein the composition further comprises a cationic surfactant system.

13. A hair conditioner composition according to claim 1 wherein the hair care composition further comprise a gel matrix comprising:

i. from about 0.1% to about 20% of one or more high melting point fatty compounds, by weight of said hair care composition;
ii. from about 0.1% to about 10% a cationic surfactant system of, by weight of said hair care composition; and
iii. at least about 20% of an aqueous carrier, by weight of said hair care composition.

* * * * *